(12) United States Patent
Cao et al.

(10) Patent No.: US 11,674,922 B2
(45) Date of Patent: Jun. 13, 2023

(54) POROUS NANOSTRUCTURED ELECTRODES FOR DETECTION OF NEUROTRANSMITTERS

(71) Applicant: INTERNATIONAL BUSINESS MACHINES CORPORATION, Armonk, NY (US)

(72) Inventors: Qing Cao, Yorktown Heights, NY (US); Hariklia Deligianni, Alpine, NJ (US); Fei Liu, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 658 days.

(21) Appl. No.: 16/684,888

(22) Filed: Nov. 15, 2019

(65) Prior Publication Data

US 2020/0080957 A1 Mar. 12, 2020

Related U.S. Application Data

(62) Division of application No. 15/626,363, filed on Jun. 19, 2017, now Pat. No. 10,900,924.

(51) Int. Cl.
*G01N 27/327* (2006.01)
*G01N 27/30* (2006.01)
(Continued)

(52) U.S. Cl.
CPC ....... *G01N 27/3277* (2013.01); *A61B 5/0031* (2013.01); *A61B 5/1468* (2013.01);
(Continued)

(58) Field of Classification Search
CPC ............ G01N 27/3277; G01N 27/301; G01N 27/304; G01N 27/308; G01N 27/36;
(Continued)

(56) References Cited

U.S. PATENT DOCUMENTS

| 4,820,386 A | 4/1989 | Laconti et al. |
| 7,881,763 B2 | 2/2011 | Brauker et al. |

(Continued)

FOREIGN PATENT DOCUMENTS

| CN | 103913495 A | 7/2014 |
| JP | 2016195748 A | 11/2016 |
| WO | 2016142844 A | 9/2016 |

OTHER PUBLICATIONS

Li et al., Graphene channel liquid container field effect transistor as pH sensor, Journal of Nanomaterials, 2014, http://dx.doi.org/10.1155/2014/547139 (Year: 2014).*

(Continued)

*Primary Examiner* — Joshua L Allen
*Assistant Examiner* — Shizhi Qian
(74) *Attorney, Agent, or Firm* — Cantor Colburn LLP; Robert Sullivan

(57) ABSTRACT

Embodiments of the invention are directed to a system for detecting neurotransmitters. A non-limiting example of the system includes a porous electrode. A system can also include a pH sensor attached to the porous electrode, wherein the pH sensor includes a sensing electrode and a reference electrode. The system can also include electronic circuitry in communication with the pH sensor.

11 Claims, 13 Drawing Sheets

(51) Int. Cl.

| | |
|---|---|
| *G01N 27/36* | (2006.01) |
| *C23C 16/40* | (2006.01) |
| *C23C 16/56* | (2006.01) |
| *C23C 16/02* | (2006.01) |
| *A61B 5/145* | (2006.01) |
| *A61B 5/1468* | (2006.01) |
| *A61B 5/00* | (2006.01) |
| *A61B 5/24* | (2021.01) |
| *H05K 3/12* | (2006.01) |

(52) U.S. Cl.
CPC ............ *A61B 5/14539* (2013.01); *A61B 5/24* (2021.01); *A61B 5/4041* (2013.01); *A61B 5/6868* (2013.01); *C23C 16/0227* (2013.01); *C23C 16/403* (2013.01); *C23C 16/56* (2013.01); *G01N 27/301* (2013.01); *G01N 27/304* (2013.01); *G01N 27/308* (2013.01); *G01N 27/36* (2013.01); *A61B 2562/0285* (2013.01); *A61B 2562/125* (2013.01); *G01N 27/302* (2013.01); *G01N 27/3278* (2013.01); *H05K 3/12* (2013.01)

(58) Field of Classification Search
CPC .............. G01N 27/302; G01N 27/3278; A61B 5/0031; A61B 5/14539; A61B 5/1468; A61B 5/24; A61B 5/4041; A61B 5/6868; A61B 2562/0285; A61B 2562/125; C23C 16/0227; C23C 16/403; C23C 16/56; H05K 3/12
See application file for complete search history.

(56) References Cited

U.S. PATENT DOCUMENTS

| | | |
|---|---|---|
| 8,007,167 B2 | 8/2011 | Cummins |
| 8,666,471 B2 | 3/2014 | Rogers et al. |
| 8,700,161 B2 | 4/2014 | Harel et al. |
| 10,761,046 B2 | 9/2020 | Papageorge et al. |
| 2007/0281156 A1* | 12/2007 | Lieber ............... H01L 21/02543 428/401 |
| 2008/0249391 A1 | 10/2008 | Moxon et al. |
| 2009/0275179 A1 | 11/2009 | Basker et al. |
| 2010/0141211 A1* | 6/2010 | Yazami ................ H01M 4/368 429/105 |
| 2011/0012085 A1 | 1/2011 | Deligianni et al. |
| 2011/0315962 A1* | 12/2011 | Lieber .................. H01L 29/267 257/E21.531 |
| 2012/0048733 A1* | 3/2012 | Yu ......................... B82Y 15/00 977/700 |
| 2012/0094192 A1* | 4/2012 | Qu .......................... B01J 13/02 216/13 |
| 2012/0214172 A1* | 8/2012 | Chen ..................... B82Y 15/00 257/29 |
| 2013/0197332 A1 | 8/2013 | Lucisano et al. |
| 2014/0162390 A1* | 6/2014 | Afzali-Ardakani .... B82Y 10/00 977/890 |
| 2016/0003761 A1 | 1/2016 | Clark et al. |
| 2016/0022185 A1 | 1/2016 | Agarwal et al. |
| 2016/0265047 A1* | 9/2016 | van Rooyen ..... B01L 3/502715 |
| 2016/0268061 A1* | 9/2016 | Wang ..................... C01G 45/02 |
| 2017/0030854 A1 | 2/2017 | Buie et al. |
| 2017/0234861 A1* | 8/2017 | Chen .................. G01N 33/1826 435/6.11 |
| 2018/0364192 A1 | 12/2018 | Cao et al. |
| 2020/0250393 A1 | 8/2020 | Tsai et al. |
| 2021/0139333 A1* | 5/2021 | Choudhary ........... H01M 4/133 |

OTHER PUBLICATIONS

Lee et al. , Development of a highly-sensitive acetylcholine sensor using a charge-transfer technique on a smart chip, Trends in Analytical Chemistry, 2009, 28(2), 196-203 (Year: 2009).*

Ye et al. Thickness-dependent strain effect on the deformation of the graphene-encapsulated Au nanoparticles, Journal of Nanomaterials, 2014, http://dx.doi.org/10.1155/2014/98967 (Year: 2014).*

Kurzweil P., Metal oxides and ion-exchanging surfaces as pH sensors in liquids: state-of-the-art and outlook, Sensors, 2009, 9, 4955-4985. (Year: 2009).*

Zhu et al. A solid-gated graphene fet sensor for PH measurements, 2015 28th IEEE International Conference on Micro Electro Mechanical Systems (MEMS), 10.1109/MEMSYS.2015.7051097 (Year: 2015).*

Hess et al., Graphene transistors with multifunctional polymer brushes for biosensing applications, ACS Applied Materials & Interfaces, 2014, 6, 9705-9710 (Year: 2014).*

Xu et al., Nanocomposites of graphene and graphene oxides: Synthesis, molecular functionalization and application in electrochemical sensors and biosensors. A review, Microchim Acta (2017) 184:1-44 (Year: 2017).*

Kumar et al., Time-dependent pH sensing phenomena using CdSe/ZnS quantum dots in EIS structure, Nanoscale Research Letters, 2014, 9, 179 (Year: 2014).*

Kuzum et al., "Transparent and flexible low noise graphene electrodes for simultaneous electrophysiology and neuroimaging" nature COmmunications, www.nature.com/naturecommunications; published Oct. 20, 2014; 10 pgs.

List of IBM Patents or Patent Applications Treated as Related; (Appendix P), Filed Nov. 15, 2019, 2 pages.

Bucher et al. "Flexible software platform for fast-scan cyclic voltammetry data acquisition and analysis." Analytical chemistry 85.21 (2013): 10344-10353.

Robinson et al. "Monitoring Rapid Chemical Communication in the Brain." Chem Rev 108.7 (2008): 2554-2584.

* cited by examiner

POROUS NANOSTRUCTURED ELECTRODES FOR DETECTION OF NEUROTRANSMITTERS

DOMESTIC PRIORITY

This application is a divisional of U.S. patent application Ser. No. 15/626,363, filed Jun. 19, 2017, the disclosure of which in incorporated by reference herein in its entirety.

BACKGROUND

The present invention generally relates to neural electrodes and more specifically, to porous nanostructured electrodes for detection of neurotransmitters.

Neurotransmitters are chemicals that transmit signals by travelling across a synapse from one neuron to another. Over 100 unique neurotransmitters have been identified to date. The detection of such neurotransmitters in the brain, for example, and the stimulation of related neurons have applicability in a number of medical contexts. For instance, a number of diseases, such as Parkinson's disease, schizophrenia, and attention deficit hyperactivity disorder (ADHD) to name a few, involve imbalances or disruptions to neurotransmitter systems.

SUMMARY

Embodiments of the present invention are directed to a method of fabricating a porous nanostructured electrode for detection of neurotransmitters. A non-limiting example of the method includes depositing an insulating layer on a silicon substrate. The method can also include depositing a nitride layer on the insulating layer. The method can also include etching a first opening and a second opening, wherein the first opening and the second opening extend into the nitride layer and the insulating layer. The method can also include forming a reference electrode in the first opening and a sensing electrode in the second opening. The method can also include depositing a metal oxide layer over the reference electrode and the sensing electrode. The method can also include forming a trench around the reference electrode and the sensing electrode, wherein the trench is bounded by the nitride layer, the metal oxide layer, and the insulating layer. The method can also include depositing a porous electrode on the metal oxide layer.

Embodiments of the invention are directed to a system for detecting neurotransmitters. A non-limiting example of the system includes a porous electrode. A system can also include a pH sensor attached to the porous electrode, wherein the pH sensor includes a sensing electrode and a reference electrode. The system can also include electronic circuitry in communication with the pH sensor.

Embodiments of the invention are directed to an electrode for neurotransmitter analysis. A non-limiting example of the electrode includes a porous electrode optionally in contact with a polymer layer. The electrode can also include a glass layer in contact with the porous electrode and optional polymer layer. The electrode can also include a reference electrode. The electrode can also include a pH sensing electrode extending from the glass layer. The exemplary electrode can be capable of measuring a current of a neurotransmitter oxidation.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIGS. 2A-2J depict a porous nanostructured electrode after various fabrication operations according to one or more embodiments of the present invention, in which:

FIG. 2A illustrates the porous nanostructured electrode after a fabrication operation according to one or more embodiments of the present invention;

FIG. 2B illustrates the porous nanostructured electrode after a fabrication operation according to one or more embodiments of the present invention;

FIG. 2C illustrates the porous nanostructured electrode after a fabrication operation according to one or more embodiments of the present invention;

FIG. 2D illustrates the porous nanostructured electrode after a fabrication operation according to one or more embodiments of the present invention;

FIG. 2E illustrates the porous nanostructured electrode after a fabrication operation according to one or more embodiments of the present invention;

FIG. 2F illustrates the porous nanostructured electrode after a fabrication operation according to one or more embodiments of the present invention;

FIG. 2G illustrates the porous nanostructured electrode after a fabrication operation according to one or more embodiments of the present invention;

FIG. 2H illustrates the porous nanostructured electrode after a fabrication operation according to one or more embodiments of the present invention;

FIG. 2I illustrates the porous nanostructured electrode after a fabrication operation according to one or more embodiments of the present invention; and FIG. 2J illustrates the porous nanostructured electrode after a fabrication operation according to one or more embodiments of the present invention.

FIGS. 4A-4B depict a porous nanostructured electrode after fabrication operations according to one or more embodiments of the present invention, in which:

FIG. 4A illustrates the porous nanostructured electrode after an exemplary fabrication operation according to one or more embodiments of the present invention; and FIG. 4B illustrates the porous nanostructured electrode after an exemplary fabrication operation according to one or more embodiments of the present invention.

Figure 1:
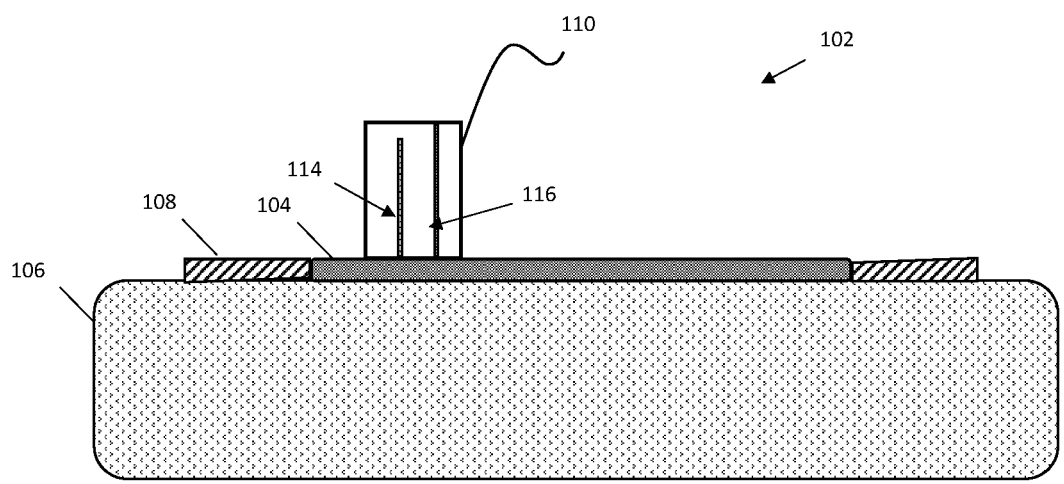
FIG. 1 depicts an exemplary system according to one or more embodiments of the present invention.

The diagrams depicted herein are illustrative. There can be many variations to the diagram or the operations described therein without departing from the spirit of the invention. For instance, the actions can be performed in a differing order or actions can be added, deleted, or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Additionally, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Spatially relative terms, e.g., "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

Turning now to an overview of technologies that are more specifically relevant to aspects of the invention, neurotransmitters are under investigation in a variety of contexts. Neurotransmitters are chemicals that allow transmission of signals from one neuron to the next by travelling across synapses. Neurotransmitters are also found at the axon endings of motor neurons, where they stimulate muscle fibers. Fluctuations of neurotransmitters in the extracellular or intracellular brain are implicated in many brain functions, including for instance cognition, behavior, and motor skills. Dopamine, for example, is a neurotransmitter implicated in neurodegenerative and psychiatric disorders such as Parkinson's disease, psychosis, and addiction. Neuroscientists have repeatedly shown, with the aid of pharmacology, that manipulations of the dopaminergic system can be crucial to treating such conditions.

In the brain, neuronal network processing can occur at a relatively high speed (i.e. sub-second speed). Moreover, because neuronal networks rely upon molecular transmission, studies of network processing can in some cases require high spatial resolution. Probing neurophysiological circuit function in the human brain at a high speed and/or at a resolution sufficient to detect molecular transmission could benefit the study of a variety of neurological disorders by providing enhanced information pertaining to the conditions at which network processing occurs.

Obtaining high-speed and high resolution information concerning neurotransmission has the potential to allow fundamental insights concerning neural circuit function to be derived, and further has the potential to foster the development of therapeutics for treatment of central nervous system (CNS) disorders. Moreover, sensing neurotransmitters at multiple electrode sites corresponding to a multiple transmitter sites in the brain can provide beneficial information about the spatial concentration gradient of a given neurotransmitter.

The study of neurotransmitters can also implicate optogenetics. Optogenetics can involve the use of light to stimulate neurons that have been genetically modified to respond to light. For deep brain tissue regions, however, localized light sources can be used to overcome challenges associated with penetration of light into the deep brain tissue regions. In such applications, electrode structures and electrodes for measuring neurotransmitters in vivo that do not impede or interfere with light transmission can be highly advantageous.

Turning now to an overview of the aspects of the invention, one or more embodiments of the invention provide electrodes for detecting neurotransmitters with high spatial resolution and high speed. Moreover, some embodiments of the invention provide electrodes suitable for in vivo optical imaging of neuronal systems. The above-described aspects of the invention improve known systems by including flexible two-dimensional (2D) electrodes to achieve increased specificity and sensitivity for the detection of neurotransmitter release using fast-scan cyclic voltammetry (FSCV). FSCV can be used for measuring sub-second changes in neurotransmitter concentration while providing high temporal and spatial resolution. According to some embodiments of the invention, electrodes can include functionally transparent graphene or metallic mesh sensor electrodes for neurotransmitter measurements using FSCV. Some embodiments of the invention can provide in-situ pH recording simultaneously with neurotransmitter measurements.

Embodiments of the invention include miniaturized electrodes including new materials for applications involving neurotransmitter detection. Neurotransmitter concentration can be measured suing FSCV to detect an oxidation current, for instance. Oxidation reactions can proceed with the release of H+ ions, resulting in a pH decrease at the surface of an electrode. For example, oxidation of dopamine can proceed according to the following reaction:

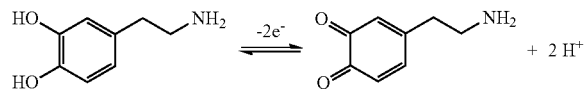

in which the flux of electrons can be detected as current and wherein the oxidation of dopamine to dopamine-o-quinone results in release of 2H+ ions. In FSCV an electrode can be used to quickly raise and lower a voltage, for instance on the sub-second scale, resulting in the repeated oxidation and reduction of a neurotransmitter in the microsecond time frame. FSCV can be used to detect changes in chemical concentration or to identify or select for particular neurotransmitters, for example based upon reduction potential.

In some embodiments of the invention, an in vivo pH measurement can be taken during neurotransmitter oxidation. Some embodiments of the invention include pH measurement using a flat bottom pH electrode placed behind a porous electrode, such as a carbon fiber electrode or a metallic mesh electrode. In some embodiments of the invention, a pH measurement uses a solid state metal-oxide biocompatible electrode.

Turning now to a more detailed description of aspects of the present invention, FIG. 1 depicts an exemplary system 102 including a porous nanostructured electrode for detection of neurotransmitters according to exemplary embodiments of the invention. As is shown in FIG. 1, the exemplary system 102 can include a porous electrode 104. The porous electrode 104 can include graphene, doped/undoped graphene, or metal mesh. In some embodiments of the invention, the porous electrode is a 2D graphene layer. The graphene layer can have a thickness, for example, of about 0.1 to about 1 nanometers (nm), such as about 0.5 to about 0.7 nm. A graphene layer can be applied to the structure, for example, by transfer printing. The porous electrode 104 can be placed in contact with biological fluid containing one or more neurotransmitters 106. The biological fluid 106 can be, for instance, brain fluid. The porous electrode can have one or more pH electrodes 110 affixed thereto. The pH electrodes can have a diameter of less than or equal to 5 microns. The pH sensor can include a sensing electrode 116 and a reference electrode 114. The system 102 can also include metal contacts 108 connected to the porous electrode 104. The metal contacts 108 can include any conductive metal useful in FSCV applications.

Reference electrode 114 can include, for instance, silver or titanium. In some embodiments of the invention, reference electrode is a silver nanowire. Sensing electrode 116 can include, for example, platinum or titanium, such as a platinum or titanium nanowire. Sensing electrode can also include metal oxide nanowires.

In some embodiments of the invention, the pH electrode 110 includes a silicon dioxide pH sensing electrode, optionally contained within an ionic solution, such as an aqueous chloride solution. In some embodiments of the invention, pH electrode includes one or more additional layers, including, for instance, an insulating layer, a polymer layer, or an oxide layer.

Exemplary systems including porous nanostructured electrodes can also include electronic circuitry, for instance, circuitry capable of performing FSCV and/or pH measurements. The electronic circuitry can be included, for example, within a silicon layer or a polymer layer in communication with the pH sensor and/or the porous electrode.

Exemplary neurotransmitters that can be detected by porous nanostructured electrodes according to embodiments of the invention can include, but are not limited to, tyrosine derivatives, such as dopamine, L-Dopa, norepinephrine, epinephrine, DOPAC, homovanillic acid, 3-methoxy-tyramine, tryptophan derivatives, such as serotonin and 5-hyroxyindolacetic acid, adenosine, ascorbic acid, and uric acid. Neurotransmitters can be detected by FSCV using electrodes according to embodiments of the invention.

Figure 2A:
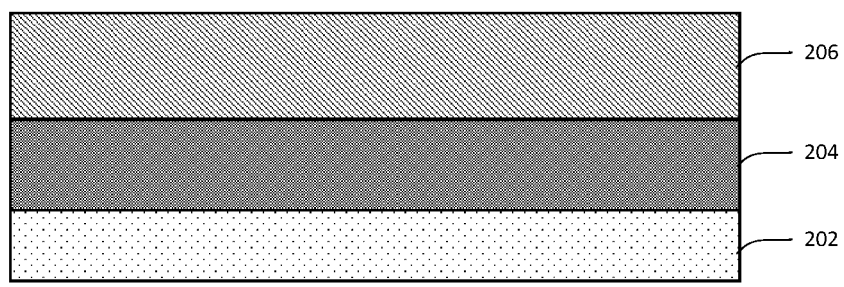

FIGS. 2A-2J illustrate an exemplary method for fabricating a porous nanostructured electrode according to embodiments of the invention. As is shown in FIG. 2A, a silicon layer 202 can be provided with an insulating layer 204, such as a silicon oxide layer. As is shown, a nitride layer 206, such as a silicon nitride layer, can be deposited on the structure, for instance, by chemical vapor deposition. The silicon layer 202, can include any silicon-based materials useful in semiconducting applications, and can be for instance a silicon wafer. In some embodiments of the invention, can include electronic circuitry, such as control circuitry for conducting FSCV or pH measurements.

Figure 2B:
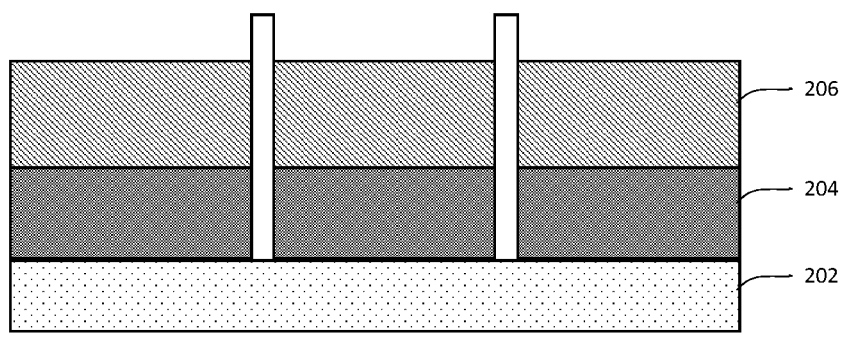

As is depicted in FIG. 2B, the exemplary method of fabrication includes etching openings or trenches in the silicon nitride layer 206 and insulating layer 204. In some embodiments of the invention, two openings, a first opening and a second opening, are formed and can be patterned and etched using standard photolithography techniques. In some embodiments of the invention, etching openings in the silicon nitride layer 206 and insulating layer 204 includes performing reactive ion etching (ME). The openings can have dimensions suitable for forming a sensing electrode and a reference electrode. For example, an opening can have a width on the nanometer scale.

Figure 2C:
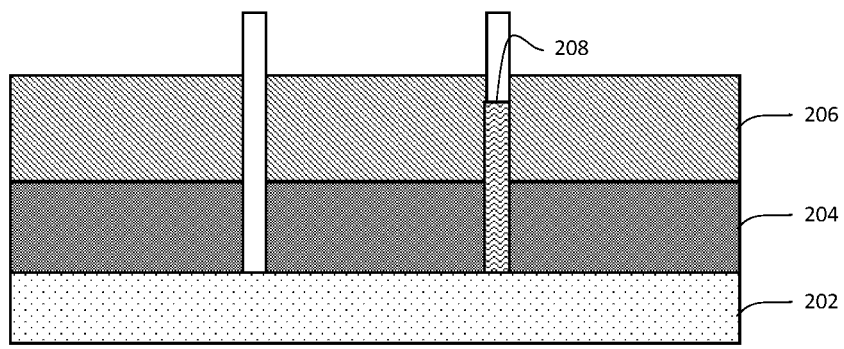
Figure 2D:
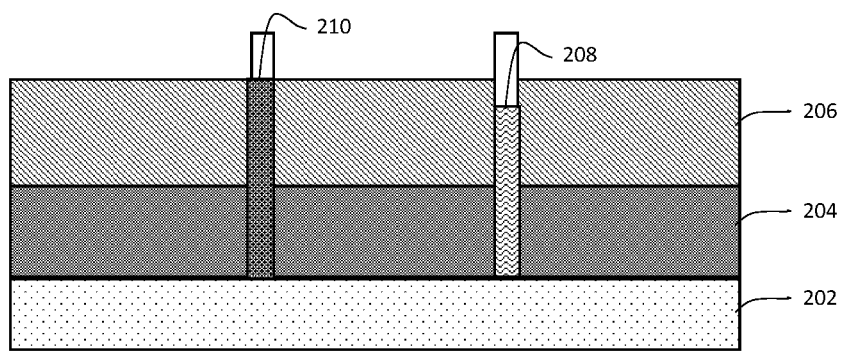

In some embodiments of the invention, as is depicted in FIG. 2C, a reference electrode material 208, such as silver, is deposited in one opening to form a reference electrode. As is depicted in FIG. 2D, a sensing electrode material 210, such as platinum, can be deposited in another opening to form a sensing electrode. In some embodiments of the invention, the structure is planarized, such as by chemical mechanical planarization (CMP). The resultant reference electrode and sensing electrode can be the same length or differing lengths.

Figure 2E:
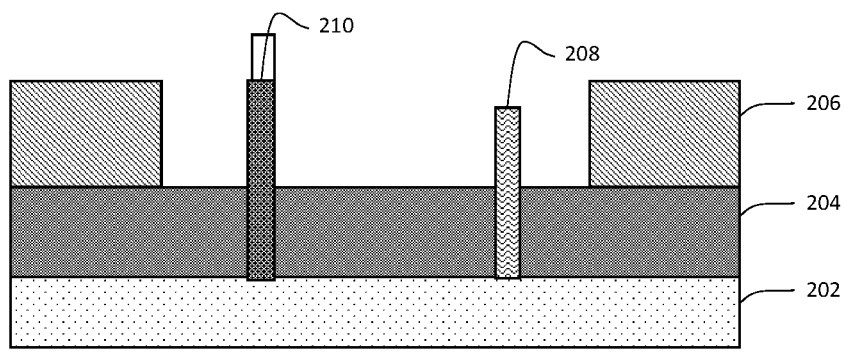

The exemplary method can include, as illustrated in FIG. 2E, selectively etching a portion of the silicon nitride layer surrounding the sensing electrode material and the reference electrode material to provide a trench. The opening can be formed by standard lithography techniques, such as by conducting a wet etch selective to silicon nitride. The trench is formed by two silicon nitride walls, each parallel to the reference electrode and sensing electrode, and the silicon oxide layer.

Figure 2F:
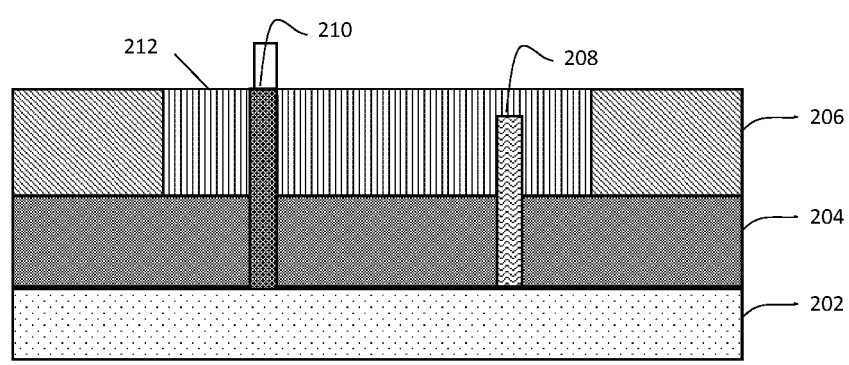

As is shown in FIG. 2F, a sacrificial layer 212 can be deposited in the trench. The sacrificial layer can include $Al_2O_3$ can be deposited, for example, by CVD.

Figure 2G:
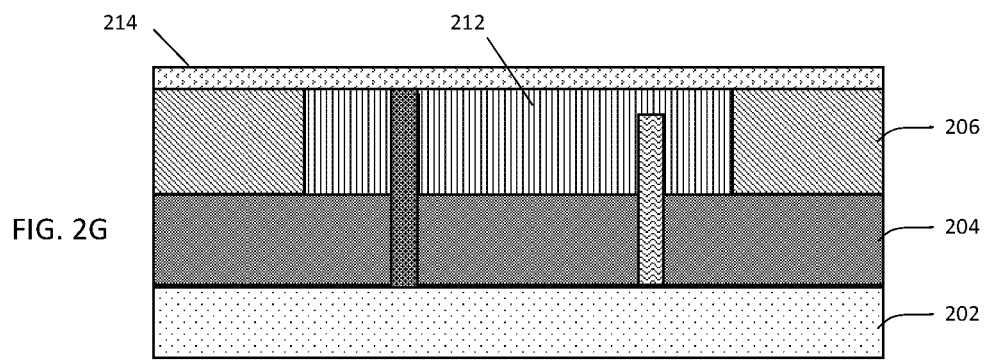

In some embodiments of the invention, as is shown in FIG. 2G, a thin metal oxide layer 214 is deposited on the structure. The thin metal oxide layer 214 can include a metal layer capable of proton exchange for pH detection in biological fluids. Thin metal oxide layer 214 can include, for instance, silver oxide, platinum oxide, ruthenium oxide, rhenium oxide, rhodium oxide, osmium oxide, palladium oxide, titanium oxide, or tantalum oxide. The thin metal oxide layer can be deposited, for example, by electrodeposition or sputtering.

Figure 2H:
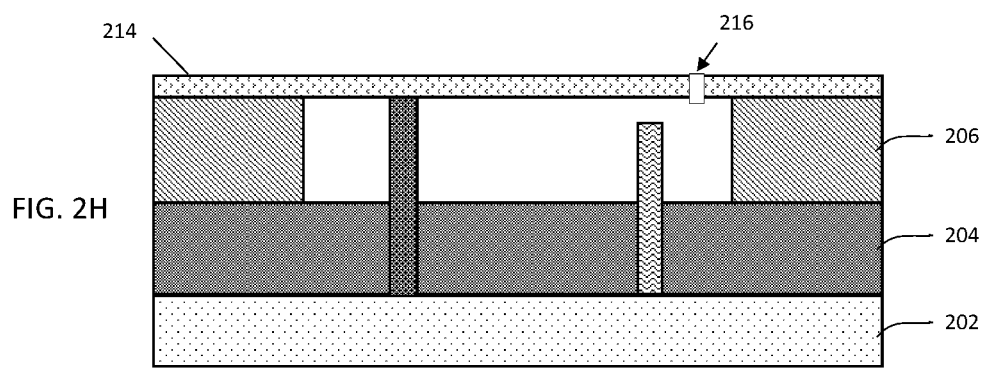

As is shown in FIG. 2H, a fourth opening can be etched into the thin metal oxide layer 214. The fourth opening can be sized to provide access to the sacrificial layer for removal of the sacrificial layer by wet etch. FIG. 2H illustrates the structure after removal of the sacrificial layer. Removal of the sacrificial layer exposes the sensing and reference electrodes and can re-establish the trench.

Figure 2I:
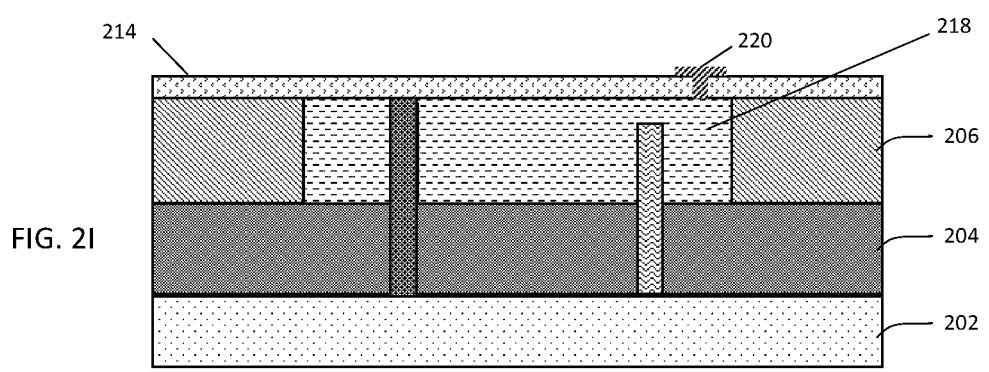
Figure 2J:
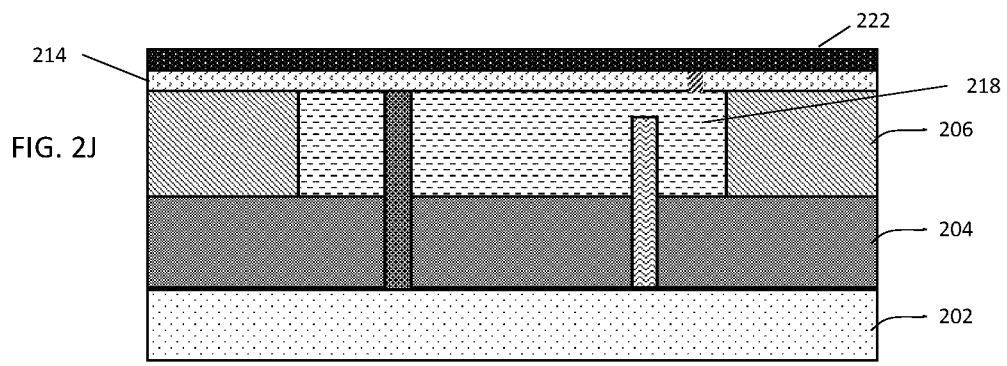

As is illustrated in FIG. 2I, in some embodiments of the invention, after removal of the sacrificial layer, the trench is filled with an ionic solution 218. The ionic solution can include, for example, hydrochloric acid (HCl) at a concentration of 0.01 to 0.2 M, such as a 0.1M solution of HCl. In some embodiments of the invention, not shown in FIG. 2I, ionic solution is not provided. For example, the porosity of the graphene layer or metal mesh can provide access to biological fluids, obviating the need for additional solution. The fourth opening can be sealed after filling the trench with ionic solution, for example, with an epoxy resin or any other material suitable for sealing the fourth opening.

In some embodiments of the invention, a graphene layer 222 is deposited on the metal oxide layer 214. In operation, for example, the graphene layer 222 can be placed in contact with biological fluid, such as fluid associated with neural tissue, for detection and analysis of neurotransmitters, such as the identity, concentration, and activity of neurotransmitters.

In some embodiments of the invention, not shown in FIGS. 2A-2J, instead of a graphene layer another porous electrode can be deposited on the structure, such as a metallic mesh. In some embodiments of the invention, a polymer layer is deposited on the metal oxide layer. Some embodiments of the invention include, instead of the metal oxide layer, a glass layer.

Figure 3:
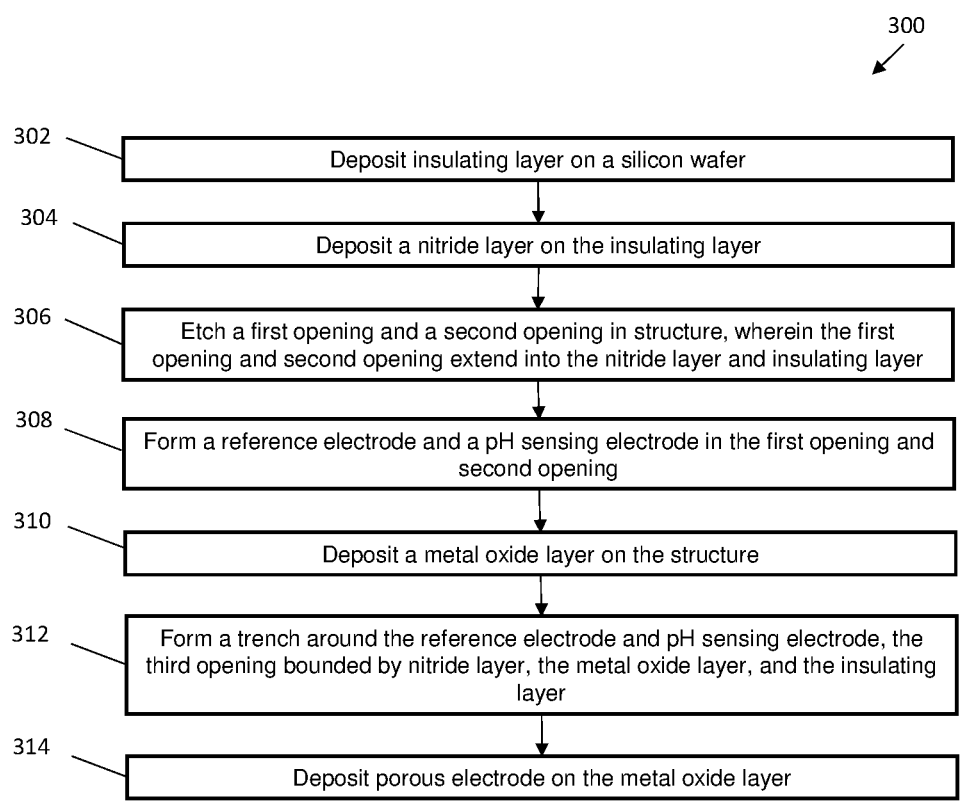
FIG. 3 depicts a flow diagram of an exemplary method of fabricating a porous nanostructured electrode according to one or more embodiments of the present invention.

FIG. 3 depicts a flow diagram of a method 300 for fabricating a porous nanostructured electrode for detection of neurotransmitters according to some embodiments of the invention. The method 300 can include depositing an insulating layer on a silicon wafer, as is shown at block 302. The method 300 can also include depositing a nitride layer on the oxide layer, as is shown at block 304. The method 300 can also include, as is shown at block 306, etching a first opening and a second opening in the structure, wherein the first opening and second opening extend through the nitride layer and oxide layer. The method 300 also includes, as shown at block 308, forming a reference electrode and a pH sensing electrode in the first opening and second opening. The method 300 also includes, as is shown at block 310, depositing a metal oxide layer on the structure. The method 300 also includes, as is shown at block 312, depositing a metal oxide layer on the structure. The method 300 can also include, as is shown at block 314, depositing a porous electrode on the metal oxide layer. The porous electrode can include, for example, a graphene layer or a metal mesh.

Figure 4A:
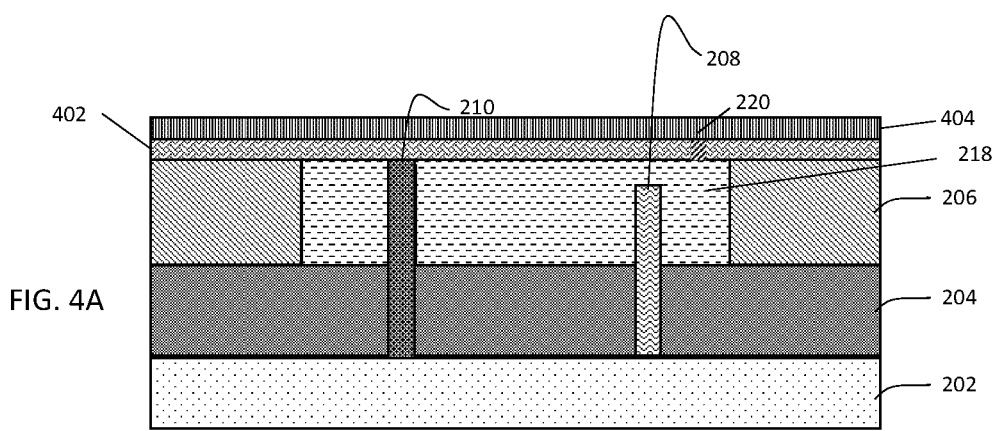
Figure 4B:
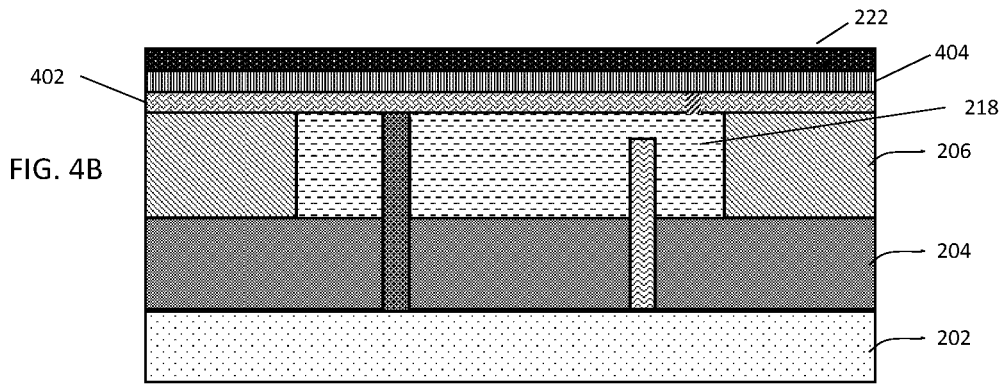

FIGS. 4A-4B illustrate another method for fabricating an exemplary porous nanostructured electrode according to some embodiments of the invention. As is shown, a structure prepared, for example, as is illustrated in FIGS. 2A-2F, can be provided. A glass layer 402 can be deposited on the structure, and the trench can be filled with an ionic solution 218, as is depicted in FIG. 4A. The glass layer, for instance, can include a silicon oxide glass membrane mesh and can have a thickness of 10 to 100 nm. Optionally, a polymer layer 404 can be deposited on the structure. Polymer layer 404 can include, for instance, an insulating polymer, such as poly di-methyl siloxane (PDMS), parylene, or poly(methyl methacrylate) (PMMA). In some embodiments of the invention, the polymer layer 404 is integrated with electronic circuitry.

As is depicted in FIG. 4B, a graphene layer can be deposited on the structure after addition of the glass layer 402 and the optional polymer layer 404.

Figure 5:
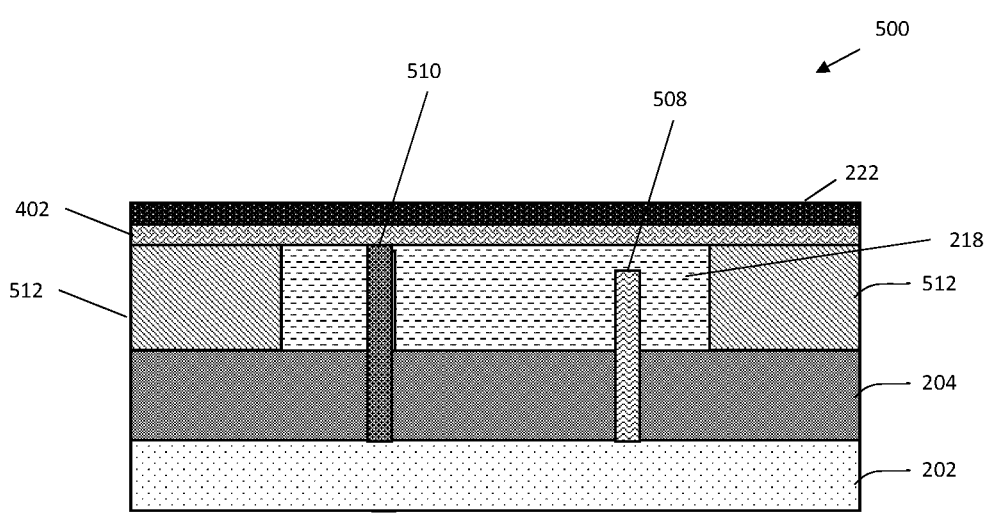
FIG. 5 depicts an exemplary electrode according to one or more embodiments of the present invention.

FIG. 5 depicts a pH electrode 500 according to exemplary embodiments of the invention. The pH electrode 500 can include a silicon substrate 202, insulating layer 204, a reference electrode 508 and a pH sensing electrode 510. The reference electrode 508 and pH sensing electrode 510 can be in an opening containing an ionic solution 218, confined to the structure by nitride walls 512 and a glass layer 402. The glass layer 402 can be in contact with the pH sensing electrode 510, the ionic solution 218, the nitride walls 512, and optionally with the reference electrode (not shown in FIG. 5). A graphene layer 222 can be included on the glass layer 402. The graphene layer 222 can include doped or undoped graphene.

Figure 6:
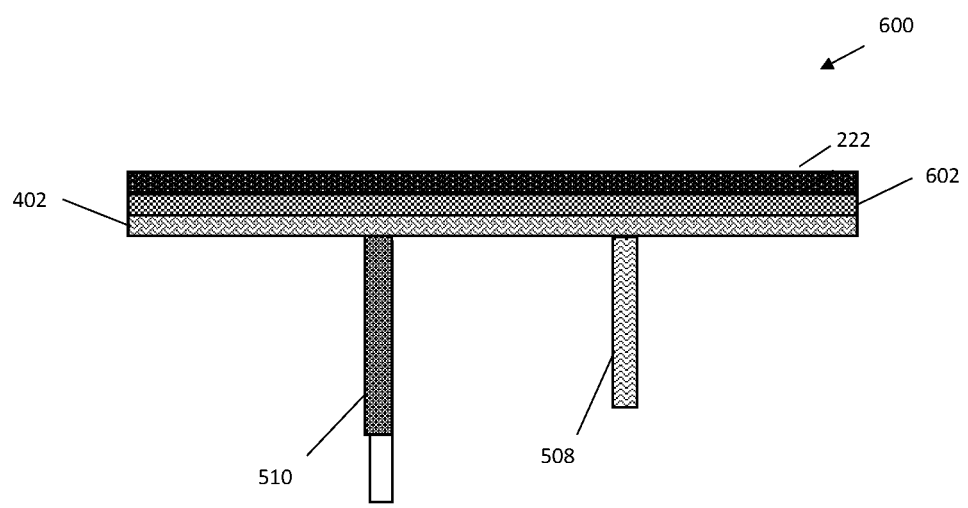
FIG. 6 depicts an exemplary electrode according to one or more embodiments of the present invention.

FIG. 6 depicts another pH electrode 600 according to exemplary embodiments of the invention. The pH electrode 600 can include a reference electrode 508 and a pH sensing electrode 510. The reference electrode 508 and pH sensing electrode 510 can be attached to a glass layer 402. The structure 600 also includes an integrated polymer layer 602.

Integrated polymer layer can include a polymer suitable for holding electronic circuitry, such as PDMS or PMMA, and can include circuitry sufficient to perform FSCV and pH sensing operations, such as a microcontroller, memory, filters, and the like. A graphene layer 222 can be included on the glass layer 402.

In some embodiments of the invention, a graphene layer is attached to metal oxide nanowires that work as pH sensors. For example, metal oxide nanowires that work as pH sensors can include silver oxide, platinum oxide, iridium oxide, ruthenium oxide, rhenium oxide, rhodium oxide, osmium oxide, palladium oxide, titanium oxide, or tantalum oxide.

Figure 7:
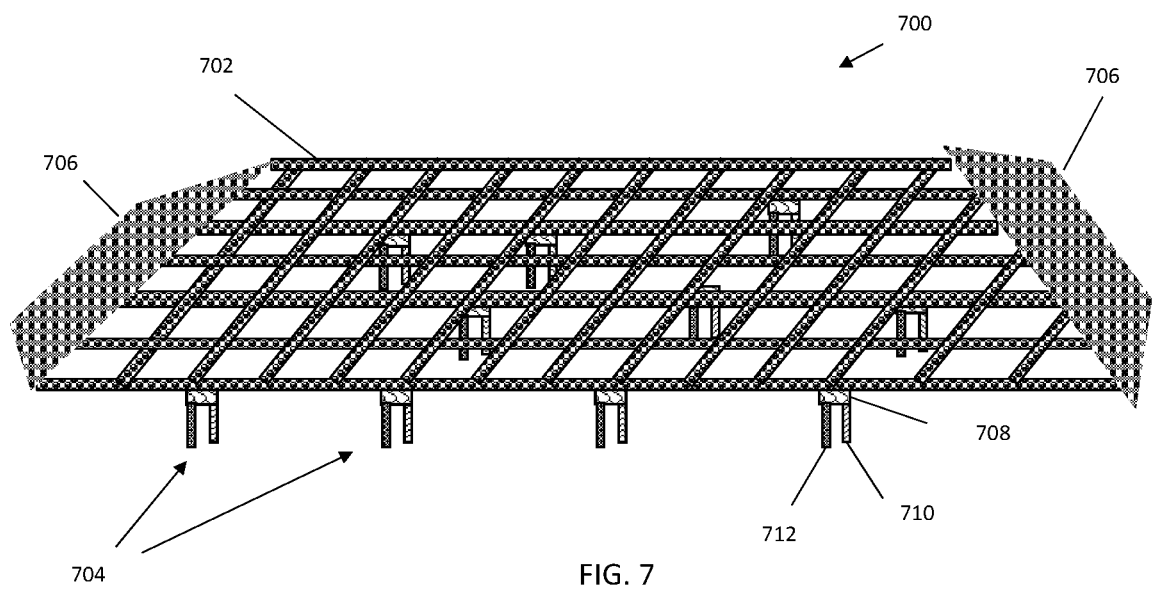
FIG. 7 depicts an exemplary system according to one or more embodiments of the present invention.

FIG. 7 depicts an exemplary system 700 for detection of neurotransmitters according to one or more embodiments of the invention. The system 700 can include a metal mesh 702. The metal mesh can include a conductive metal, such as silver, gold, platinum, iridium, rhodium, palladium, rhenium, osmium, tungsten, titanium, tantalum, and/or alloys thereof. The metal mesh can be prepared by any known method, such as by electroforming or electroplating. The system 700 can also include metal contacts 706 in contact with the metal mesh 702. The system 700 can also include metal oxide nanowire-pH sensors 704. The metal oxide nanowire-pH sensors 704 can include a metal oxide 708, such as silver oxide, platinum oxide, ruthenium oxide, rhenium oxide, rhodium oxide, osmium oxide, palladium oxide, titanium oxide, or tantalum oxide. The metal oxide nanowire-pH sensors 704 can also include a pH sensing electrode 712, such as platinum or titanium electrode, and a reference electrode 710. In operation, for example, the system 700 can be placed in contact with brain fluid. The metal-oxide nanowire-pH sensors can detect a voltage difference proportional to pH and can identify, through FSCV, neurotransmitter characteristics, identity, and/or concentration.

In some embodiments of the invention, the system 700 of FIG. 7 includes doped or undoped silicon dioxide nanowires in place of the metal oxide nanowires.

In some embodiments of the invention, the system 700 of FIG. 7 can include graphene in place of the metal mesh 702.

Figure 8:
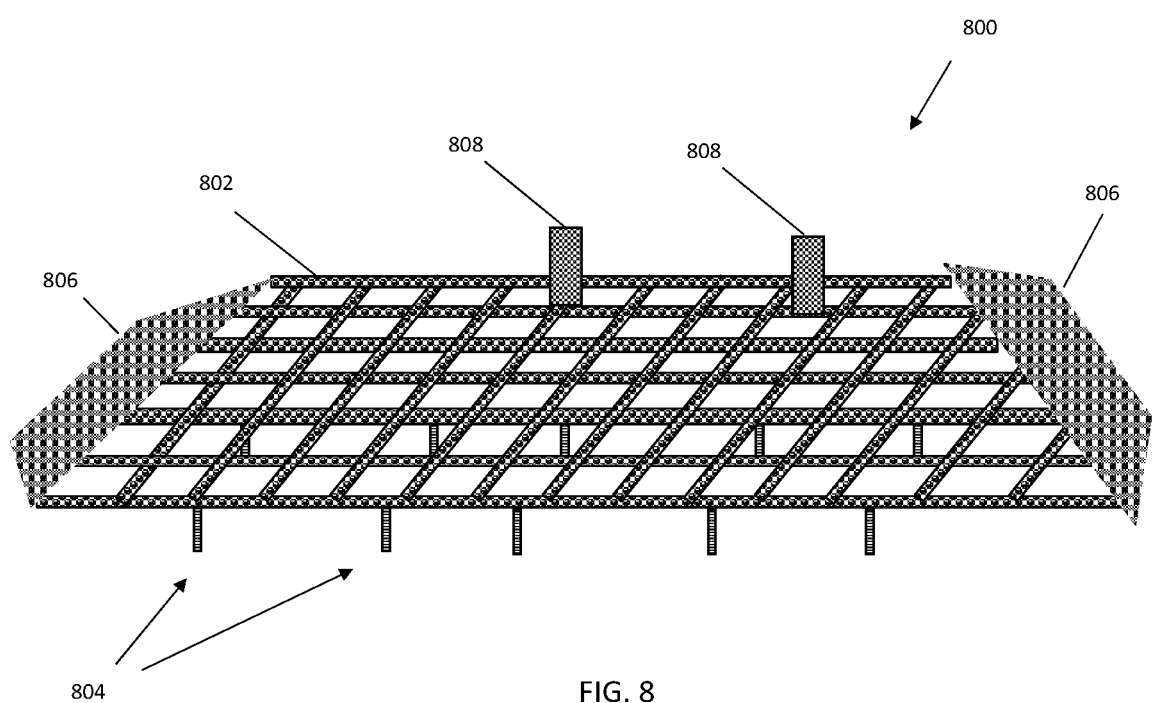
FIG. 8 depicts an exemplary system according to one or more embodiments of the present invention.

FIG. 8 depicts another exemplary system 800 for detection of neurotransmitters according to one or more embodiments of the invention. The system 800 can include a metal mesh 802. The metal mesh can include a conductive metal, such as silver, gold, platinum, iridium, rhodium, palladium, rhenium, osmium, tungsten, titanium, tantalum, and/or alloys thereof. The metal mesh can be prepared by any known method, such as by electroforming or electroplating. The system 800 can also include nanowires 804 in contact with the metal mesh 802. The nanowires 804 can include, for example, a nanowire including a metal oxide or a doped or undoped silicon nanowire. The system 800 can also include pH sensors 808. The pH sensors 808 can include, for instance, a flat bottomed silicon dioxide pH electrode including aqueous solution and a pH sensing electrode and a reference electrode. The system can also include metal contacts 806 adjacent to the metal mesh 802. In some embodiments of the invention, not shown in FIG. 8, the system 800 can include a graphene layer in place of the metal mesh 802. The nanowires can have a diameter, for instance, of 10 to 15 nanometers (nm) and can be fabricated by known methods. In some embodiments of the invention, the nanowires are integrated with the metal mesh 802 (or a graphene layer).

In operation, for example, the system 800 of FIG. 8 can be placed in contact with a biological fluid, such as a brain fluid, that includes dopamine and/or other neurotransmitters. The nanowires can be used to detect dopamine and/or other neurotransmitters with high selectivity, for instance due to the high polarization of the nanowires and the relatively high surface area of the nanowire-metal mesh structure.

Figure 9:
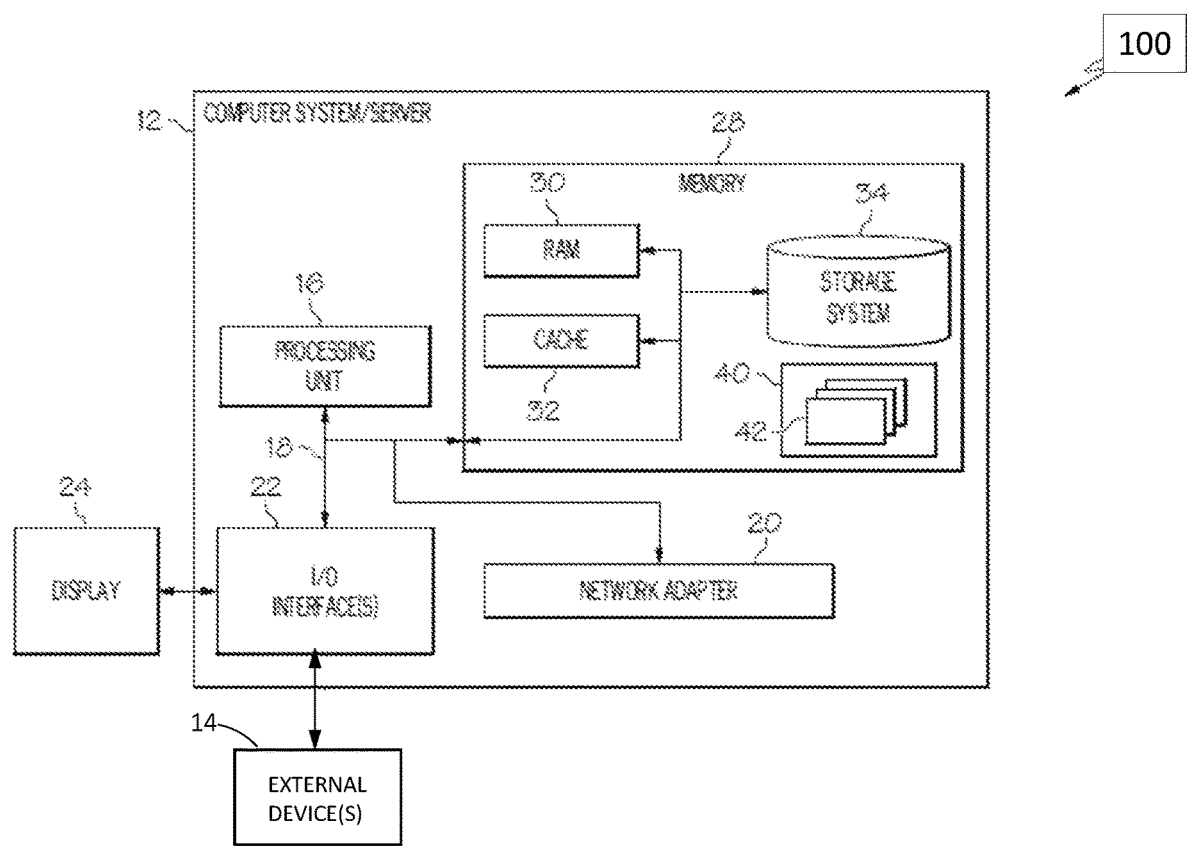
FIG. 9 depicts an exemplary computing system node according to one or more embodiments of the present invention.

FIG. 9 depicts a computing system node 100 according to one or more embodiments of the present invention. Computer system/server 12 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Deposition is any process that grows, coats, or otherwise transfers a material onto the wafer. Available technologies include, but are not limited to, thermal oxidation, physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and CMP, etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography, nanoimprint lithography, and reactive ion etching.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A system for detecting neurotransmitters, the system comprising:
   a porous electrode;
   a pH sensor attached to the porous electrode, wherein the pH sensor comprises a sensing electrode, a reference electrode, and a metal oxide layer, wherein proximal ends of the reference electrode and the sensing electrode are in direct contact with a distal end of the metal oxide layer and the porous electrode is in direct contact with a proximal end of the metal oxide layer; and
   electronic circuitry in communication with the pH sensor.

2. The system according to claim 1, wherein the porous electrode comprises a graphene layer.

3. The system according to claim 2, wherein the graphene layer has a thickness of about 0.1 nm to about 1 nm.

4. The system according to claim 2, wherein the graphene layer is doped.

5. The system according to claim 1, wherein the porous electrode is metal mesh.

6. The system according to claim 5, wherein the metal mesh comprises a metal selected from the group consisting of silver, gold, platinum, iridium, rhodium, palladium, rhenium, osmium, tungsten, titanium, tantalum, and alloys thereof.

7. The system according to claim 1, further comprising a polymer layer in contact with the porous electrode.

8. The system according to claim 1, wherein the metal oxide layer is selected from the group consisting of silver oxide, platinum oxide, ruthenium oxide, rhenium oxide, rhodium oxide, osmium oxide, palladium oxide, titanium oxide, and tantalum oxide.

9. The system according to claim 1, wherein at least one of the sensing electrode and the reference electrode comprises a plurality of nanowires.

10. The system according to claim 9, wherein the plurality of nanowires comprise a metal oxide.

11. The system according to claim 9, wherein the plurality of nanowires comprise doped or undoped silicon.

* * * * *